(12) United States Patent
Panula et al.

(10) Patent No.: US 12,390,116 B2
(45) Date of Patent: Aug. 19, 2025

(54) APPARATUS FOR MEASURING FUNCTIONALITY OF AN ARTERIAL SYSTEM

(71) Applicant: TURUN YLIOPISTO, Turun yliopisto (FI)

(72) Inventors: Tuukka Panula, Turun yliopisto (FI); Matti Kaisti, Turun yliopisto (FI); Mikko Pänkäälä, Turun yliopisto (FI); Tero Koivisto, Turun yliopisto (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 0 days.

(21) Appl. No.: 18/602,179

(22) Filed: Mar. 12, 2024

(65) Prior Publication Data

US 2024/0206751 A1 Jun. 27, 2024

Related U.S. Application Data

(62) Division of application No. 17/421,514, filed as application No. PCT/FI2019/050807 on Nov. 13, 2019, now Pat. No. 12,274,537.

(30) Foreign Application Priority Data

Jan. 9, 2019 (FI) ........................ 20195009

(51) Int. Cl.
*A61B 5/024* (2006.01)
*A61B 5/00* (2006.01)
(Continued)

(52) U.S. Cl.
CPC ...... *A61B 5/02416* (2013.01); *A61B 5/02108* (2013.01); *A61B 5/02141* (2013.01);
(Continued)

(58) Field of Classification Search
CPC ............ A61B 5/02416; A61B 5/02108; A61B 5/02141; A61B 5/02241; A61B 5/02255;
(Continued)

(56) References Cited

U.S. PATENT DOCUMENTS 5,388,585 A * 2/1995 Tomita ................. A61B 5/0225
600/494
5,450,852 A * 9/1995 Archibald .......... A61B 5/02116
600/500
(Continued)

FOREIGN PATENT DOCUMENTS

EP 1992282 A1 11/2008
EP 2732759 A1 5/2014
(Continued)

OTHER PUBLICATIONS

Office Action, issued in Korean Patent Application No. 10-2021-7020896 dated Jun. 21, 2024.
(Continued)

*Primary Examiner* — Oommen Jacob
(74) *Attorney, Agent, or Firm* — NIXON & VANDERHYE

(57) ABSTRACT

An apparatus for measuring functionality of an arterial system of an individual includes a photoplethysmography sensor for emitting, to the arterial system, electromagnetic radiation having a wavelength in the range from 475 nm to 600 nm and for receiving a part of the electromagnetic radiation reflected off the arterial system. The apparatus further includes a pressure instrument for managing mechanical pressure applied on the arterial system when the photoplethysmography sensor emits and receives the electromagnetic radiation to and from the arterial system. The effect of the mechanical pressure on the envelope of the reflected electromagnetic radiation can be used for deter-
(Continued)

mining diastolic blood pressure of arteries or for determining whether there is normal endothelial function.

16 Claims, 7 Drawing Sheets

(51) Int. Cl.
 *A61B 5/021* (2006.01)
 *A61B 5/022* (2006.01)
 *A61B 5/0225* (2006.01)
 *A61B 5/1455* (2006.01)

(52) U.S. Cl.
 CPC ...... *A61B 5/02241* (2013.01); *A61B 5/02255* (2013.01); *A61B 5/14551* (2013.01); *A61B 5/6826* (2013.01); *A61B 5/6843* (2013.01)

(58) Field of Classification Search
 CPC . A61B 5/14551; A61B 5/6826; A61B 5/6843; A61B 5/022
 See application file for complete search history.

(56) References Cited

U.S. PATENT DOCUMENTS

| | | | | |
|---|---|---|---|---|
| 6,322,515 | B1* | 11/2001 | Goor | A61B 5/6838 600/483 |
| 6,402,696 | B1* | 6/2002 | Nitzan | A61B 5/7242 600/490 |
| 6,908,436 | B2* | 6/2005 | Chowienczyk | A61B 5/026 600/500 |
| 7,029,448 | B2* | 4/2006 | Kubo | A61B 5/0225 600/490 |
| 8,016,761 | B2* | 9/2011 | Friedman | A61B 5/022 600/490 |
| 8,057,400 | B2* | 11/2011 | Parfenov | A61B 5/022 600/500 |
| 2002/0188206 | A1* | 12/2002 | Davis | A61B 5/022 600/490 |
| 2003/0065269 | A1* | 4/2003 | Vetter | A61B 5/02416 600/503 |
| 2008/0119741 | A1* | 5/2008 | Friedman | A61B 5/02125 600/485 |
| 2008/0132769 | A1* | 6/2008 | Henderson | A61B 5/021 600/301 |
| 2009/0143655 | A1 | 6/2009 | Shani | |
| 2009/0259131 | A1* | 10/2009 | Tsuji | A61B 5/022 600/493 |
| 2009/0312651 | A1* | 12/2009 | Sano | A61B 5/02141 600/493 |
| 2010/0268092 | A1* | 10/2010 | Kobayashi | A61B 5/02125 600/483 |
| 2011/0054277 | A1* | 3/2011 | Pinter | A61B 5/02125 600/529 |
| 2011/0066048 | A1* | 3/2011 | Tsuji | A61B 5/02 600/490 |
| 2011/0105917 | A1* | 5/2011 | Fortin | A61B 5/0059 600/490 |
| 2011/0152650 | A1 | 6/2011 | Donehoo | |
| 2012/0059233 | A1 | 3/2012 | Huber | |
| 2012/0215082 | A1* | 8/2012 | Chen | A61B 5/02108 600/335 |
| 2012/0215118 | A1 | 8/2012 | Chen et al. | |
| 2013/0303923 | A1* | 11/2013 | Lerner | A61B 5/02208 600/490 |
| 2013/0324866 | A1* | 12/2013 | Gladshtein | A61B 5/0535 600/507 |
| 2014/0142434 | A1* | 5/2014 | Nitzan | A61B 5/02108 600/480 |
| 2014/0142445 | A1 | 5/2014 | Banet | |
| 2014/0257062 | A1 | 9/2014 | Masin | |
| 2015/0065826 | A1* | 3/2015 | Mulligan | A61B 5/7246 600/323 |
| 2015/0216425 | A1* | 8/2015 | Gladshtein | A61B 5/02416 600/407 |
| 2015/0250394 | A1 | 9/2015 | Ono | |
| 2015/0265166 | A1 | 9/2015 | Tanaka | |
| 2015/0359437 | A1* | 12/2015 | Maltz | A61B 5/6828 600/481 |
| 2016/0081627 | A1* | 3/2016 | McGloin | G16H 50/30 600/595 |
| 2017/0095168 | A1 | 4/2017 | Kwon et al. | |
| 2017/0188850 | A1 | 7/2017 | Banet | |
| 2018/0206746 | A1* | 7/2018 | Narasimhan | A61B 5/02241 |
| 2018/0235468 | A1 | 8/2018 | Khachaturian | |
| 2019/0313979 | A1* | 10/2019 | Kang | A61B 5/02433 |
| 2019/0336016 | A1* | 11/2019 | Zhao | A61B 5/7203 |
| 2022/0061687 | A1* | 3/2022 | Panula | A61B 5/02141 |

FOREIGN PATENT DOCUMENTS

| | | |
|---|---|---|
| JP | H06169892 A | 6/1994 |
| JP | H1170087 A | 3/1999 |
| JP | 2005131356 A | 5/2005 |
| JP | 2009285029 A | 12/2009 |
| JP | 2015167685 A | 9/2015 |
| JP | 2016007312 A | 1/2016 |
| JP | 7418028 B2 | 1/2024 |
| WO | 2011051819 A1 | 5/2011 |
| WO | 2012087634 A2 | 6/2012 |
| WO | 2014054788 A1 | 4/2014 |
| WO | 2017152098 A1 | 9/2017 |
| WO | 2017169786 A1 | 10/2017 |

OTHER PUBLICATIONS

Office Action, issued in Japanese Patent Application No. 2023-172516 dated Aug. 20, 2024.
International Search Report for PCT/FI2019/050807, dated Jan. 30, 2020, 4 pages.
Office Action issued in Japanese Patent Application No. 2021-540018 dated Jul. 4, 2023.
Search Report for FI20195009 dated Jun. 19, 2019, 3 pages.
Written Opinion of the International Search Authority for PCT/FI2019/050807, dated Jan. 30, 2020, 9 pages.

* cited by examiner

APPARATUS FOR MEASURING FUNCTIONALITY OF AN ARTERIAL SYSTEM

CROSS REFERENCE TO RELATED APPLICATIONS

This application is a Divisional of application Ser. No. 17/421,514, filed on Jul. 8, 2021, which is the National Phase under 35 U.S.C. § 371 of International Application No. PCT/FI2019/050807, filed on Nov. 13, 2019, which claims the benefit under 35 U.S.C. § 119(a) to Patent Application No. 20195009, filed in Finland on Jan. 9, 2019, all of which are hereby expressly incorporated by reference into the present application.

FIELD OF THE DISCLOSURE

The disclosure relates to an apparatus and a method for measuring functionality of an arterial system. The measured functionality can be for example diastolic blood pressure "DBP" of arteries or an endothelial function that describes the ability of blood circulation to react to vasomotoric changes. Furthermore, the disclosure relates to a computer program for measuring functionality of an arterial system.

BACKGROUND

Abnormalities that may occur in an arterial system, if not diagnosed and appropriately treated and/or remedied, may progressively decrease the health of an individual. For example, elevated blood pressure is a significant risk factor for cardiovascular diseases. Therefore, a blood pressure measurement is a routine task in many medical examinations. Automated Non-Invasive Blood Pressure "NIBP" measurement techniques, a typical being the oscillometric method, have been around for decades. In this technique, a cuff is placed on top of the brachial artery and, when air is pumped into the cuff to exceed the systolic pressure, the flow of blood is completely blocked. When the air pressure in the cuff is released, pulsations i.e. oscillations measured in the cuff increase to the point of mean arterial pressure "MAP" and start to decrease after this. A bell-shaped envelope of the pulsations is presented in the time domain along with the corresponding decreasing pressure curve. Systolic and diastolic blood pressures are then computed from the MAP using pre-fixed percentages derived from population studies. The systolic blood pressure is typically deemed to correspond to a point of the pressure curve where the pressure is higher than the MAP and a value of the envelope is 50% of the maximum of the envelope i.e. 50% of the value of the envelope corresponding to the MAP, and the diastolic blood pressure is typically deemed to correspond to a point of the pressure curve where the pressure is lower than the MAP and a value of the envelope is 80% of the maximum of the envelope.

Another example of abnormalities in an arterial system is endothelial dysfunction that is concerned to be a precursor state for atherosclerosis, which is caused by formation of plaque in arteries. In clinical tests endothelial function is triggered by occluding the brachial artery for several minutes, and when released, the flow of blood in to the arteries increases and the endothelial cells start to excrete nitric oxide NO. The nitric oxide then causes the arteries to dilate letting more blood flow through. Arteries with endothelial dysfunction do not dilate in the same way.

In many cases it is advantageous that abnormalities of the kind described above are detected at an early stage. Therefore, there is a need for easy-to-use techniques for e.g. measuring blood pressure and/or for obtaining indications of endothelial dysfunction.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new apparatus for measuring functionality of an arterial system of an individual. An apparatus according to the invention comprises a photoplethysmography "PPG" sensor for emitting, to the arterial system, electromagnetic radiation having a wavelength in the range from 475 nm to 600 nm and for receiving a part of the electromagnetic radiation reflected off the arterial system. The apparatus further comprises a pressure instrument for managing mechanical pressure applied on the arterial system when the photoplethysmography sensor emits and receives the electromagnetic radiation to and from the arterial system. The pressure instrument is suitable for changing the mechanical pressure applied on the arterial system when the photoplethysmography sensor emits and receives the electromagnetic radiation to and from the arterial system, and the apparatus comprises a processing system for controlling the pressure instrument to increase the mechanical pressure until an envelope of the reflected electromagnetic radiation drops down to substantially zero and subsequently to keep the mechanical pressure constant, wherein the processing system is configured to detect whether the envelope of the reflected electromagnetic radiation increases when the mechanical pressure is kept constant, an increase of the envelope being indicative of normal endothelial function of the arterial system.

In this document, the verb "to manage" is to be understood in a broad sense so that managing does not necessarily comprise controlling or changing an entity being managed, e.g. the above-mentioned mechanical pressure, but the managing may comprise only measuring the managed entity.

The above-mentioned wavelength range from 475 nm to 600 nm has been selected so that the above-mentioned electromagnetic radiation does not reach the arteries located in the hypodermis but can only reach the more superficial dermal arterioles located in the reticular dermis. The wavelength can be, for example but not necessarily, circa 537 nm in which case the electromagnetic radiation is green light.

The pulse pressure, i.e. the difference between systolic and diastolic blood pressures, increases from the brachial artery located in an upper arm to the radial artery located in a wrist to the transverse palmar arch artery located in a fingertip. When entering the arterioles and finally the capillaries, the mean arterial pressure "MAP" and the pulse pressure drop significantly. In has been noticed that the diastolic blood pressure in the arteries of a fingertip equals substantially the systolic blood pressure of the arterioles of the fingertip. Thus, the above-described apparatus can be used for measuring the MAP in the arterioles and the systolic blood pressure in the arterioles, as well as for estimating the diastolic blood pressure in the arteries. A measurement routine may comprise, for example but not necessarily, ramping mechanical pressure applied on a fingertip and recoding the output signal of the PPG sensor. The output signal of the PPG sensor is indicative of electromagnetic radiation reflected off the arterioles of the fingertip. The MAP corresponds to a value of the mechanical pressure at which the envelope of the reflected electromagnetic radiation reaches its maximum. The systolic blood pressure in the arterioles and the diastolic blood pressure in the arteries correspond to a value of the mechanical pressure which is greater than the MAP and at which the envelope of the reflected electromagnetic radiation is a predetermined percentage, e.g. 50%, of the maximum. The ramping the mechanical pressure may comprise for example pressing the finger above systolic blood pressure so that the blood flow is blocked and then slowly reducing the press. It is also possible that the mechanical pressure is increased from zero up to a point at which the blood flow is blocked. The envelope of the reflected electromagnetic radiation can be formed by e.g. bandpass filtering the output signal of the PPG sensor and by constructing an envelope curve of the bandpass filtered output signal.

For another example, the above-described apparatus can be used for measuring endothelial function. A measurement routine may comprise, for example but not necessarily, increasing mechanical pressure applied on a fingertip until the envelope of the reflected electromagnetic radiation gets nearly zero and then keeping the mechanical pressure constant. In a case of proper endothelial function, an increase in the envelope of the reflected electromagnetic radiation can be seen when the mechanical pressure is kept constant. In a case of endothelial dysfunction, no increase of the kind mentioned above takes place.

In an apparatus according to an exemplifying and non-limiting embodiment, the PPG sensor comprises means for emitting, to an arterial system, second electromagnetic radiation having a wavelength in the range from 620 nm to 900 nm in addition to the above-mentioned first electromagnetic radiation having the wavelength in the range from 475 nm to 600 nm, and means for receiving parts of the above-mentioned first and second electromagnetic radiations reflected off the arterial system.

The wavelength range of the second electromagnetic radiation from 620 nm to 900 nm has been selected so that the second electromagnetic radiation reach the arteries located in the hypodermis. Thus, the second electromagnetic radiation can be used for measuring the MAP in the arteries, the systolic blood pressure in the arteries, as well as the diastolic blood pressure in the arteries. Thus, the diastolic blood pressure in the arteries can be measured with both the first and second electromagnetic radiations, which improve the accuracy and reliability of the measurement. A measurement routine may comprise, for example but not necessarily, ramping mechanical pressure applied on a fingertip and recoding, from the PPG sensor, first and second output signals corresponding to the first and second electromagnetic radiations reflected off the arterial system of the fingertip. For another example, the second electromagnetic radiation can be used for determining a point up to which the mechanical pressure applied on a fingertip is increased when measuring endothelial function. In this measurement, the mechanical pressure is increased until the envelope of the reflected second electromagnetic radiation reaches its maximum. The wavelength of the second electromagnetic radiation can be, for example but not necessarily, circa 660 nm in which case the second electromagnetic radiation is red light or circa 880 nm in which case the second electromagnetic radiation is infrared "IR" radiation.

In accordance with the invention, there is provided a new method for measuring functionality of an arterial system of an individual. A method according to the invention comprises:

emitting, to the arterial system, electromagnetic radiation having a wavelength in the range from 475 nm to 600 nm, receiving a part of the electromagnetic radiation reflected off the arterial system, changing mechanical pressure applied on the arterial system when the electromagnetic radiation is emitted to the arterial system and the reflected electromagnetic radiation is received from the arterial system so that the mechanical pressure is increased until an envelope of the reflected electromagnetic radiation drops down to substantially zero, keeping the mechanical pressure constant after the envelope of the reflected electromagnetic radiation has dropped down to substantially zero, and detecting whether the envelope of the reflected electromagnetic radiation increases when the mechanical pressure is kept constant, an increase of the envelope being indicative of normal endothelial function of the arterial system.

In accordance with the invention, there is provided also a new computer program for measuring functionality of an arterial system of an individual. A computer program according to the invention comprises computer executable instructions for controlling a programmable processing system to:

control a photoplethysmography sensor to emit, to the arterial system, electromagnetic radiation having a wavelength in the range from 475 nm to 600 nm, and to receive a part of the electromagnetic radiation reflected off the arterial system, control a pressure instrument to manage mechanical pressure applied on the arterial system when the photoplethysmography sensor emits and receives the electromagnetic radiation to and from the arterial system so that the mechanical pressure is increased until an envelope of the reflected electromagnetic radiation drops down to substantially zero, keep the mechanical pressure constant after the envelope of the reflected electromagnetic radiation has dropped down to substantially zero, and detect whether the envelope of the reflected electromagnetic radiation increases when the mechanical pressure is kept constant, an increase of the envelope being indicative of normal endothelial function of the arterial system.

In accordance with the invention, there is provided also a new computer program product. The computer program product comprises a non-volatile computer readable medium, e.g. a compact disc "CD", encoded with a computer program according to the invention.

Exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying embodiments when read in conjunction with the accompanying drawings.

The verbs "to comprise" and "to include" are used in this document as open limitations that neither exclude nor require the existence of also un-recited features. The features recited in the accompanied dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments and their advantages are explained in greater detail below with reference to the accompanying drawings, in which.

DESCRIPTION OF EXEMPLIFYING AND NON-LIMITING EMBODIMENTS

The specific examples provided in the description below should not be construed as limiting the scope and/or the applicability of the appended claims. Lists and groups of examples provided in the description are not exhaustive unless otherwise explicitly stated.

Figure 1A:
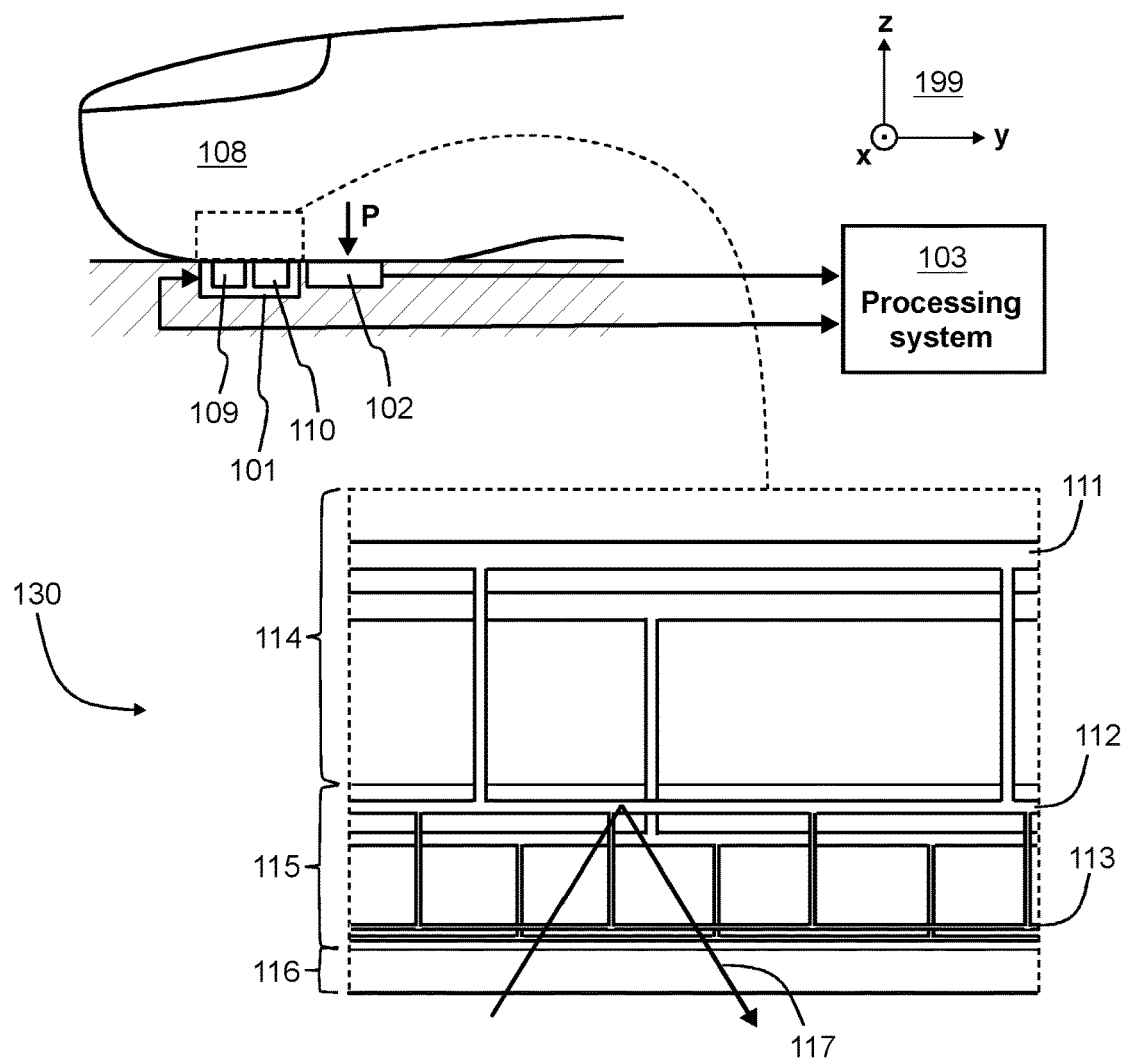
FIG. 1a illustrates an apparatus according to an exemplifying and non-limiting embodiment for measuring functionality of an arterial system.

FIG. 1a shows a schematic illustration of an apparatus according to an exemplifying and non-limiting embodiment for measuring functionality of an arterial system. The apparatus comprises a photoplethysmography "PPG" sensor 101 for emitting, to a fingertip 108 of an individual, electromagnetic radiation having a wavelength in the range from 475 nm to 600 nm and for receiving a part of the electromagnetic radiation reflected off the arterial system of the fingertip 108. In an apparatus according to an exemplifying and non-limiting embodiment, the wavelength is in the range from 480 nm to 600 nm. In an apparatus according to an exemplifying and non-limiting embodiment, the wavelength is in the range from 500 nm to 600 nm. In an apparatus according to an exemplifying and non-limiting embodiment, the wavelength is in the range from 500 nm to 575 nm. In an apparatus according to an exemplifying and non-limiting embodiment, the wavelength is in the range from 500 nm to 550 nm. The wavelength can be, for example but not necessarily, circa 537 nm in which case the electromagnetic radiation is green light. The PPG sensor 101 comprises a radiation emitter 109 and a photodetector 110. The radiation emitter 109 can be e.g. a light emitting diode "LED" and the photodetector 110 can be e.g. a photodiode or a phototransistor. FIG. 1a shows also a magnified, schematic section view 130 of the fingertip. The section plane is parallel with the yz-plane of a coordinate system 199. In the section view 130, the emitted and reflected radiation is depicted with a polyline 117. As illustrated in the section view 130, the electromagnetic radiation 117 does not reach arteries 111 located in the hypodermis 114 but can only reach arterioles 112 located in the reticular dermis 115. In the section view 130, capillaries are denoted with a reference 113 and the epidermis of the skin of the fingertip is denoted with a reference 116.

The apparatus further comprises a pressure instrument 102 for managing mechanical pressure applied on the arterial system when the photoplethysmography sensor 101 emits and receives the electromagnetic radiation. In this exemplifying case, the pressure instrument 102 comprises a pressure sensor for measuring mechanical pressure P directed by the fingertip 108 to the pressure sensor.

Figure 1B:
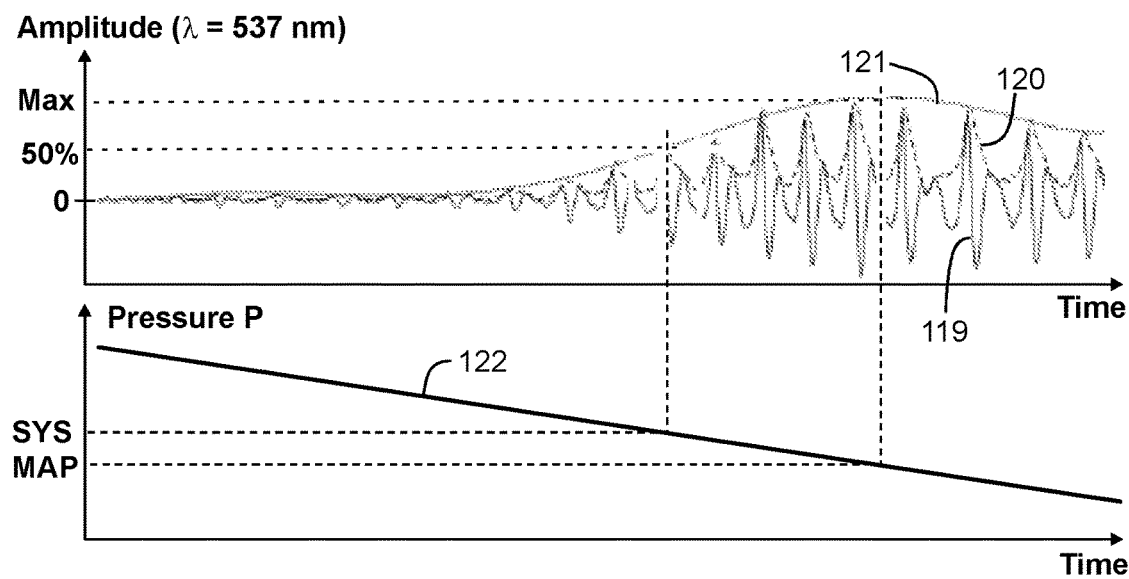
FIG. 1b shows an exemplifying graph illustrating electromagnetic radiation reflected off an arterial system of a fingertip as a function of time.

FIG. 1b shows a curve 119 that illustrates the reflected electromagnetic radiation in an exemplifying situation where the apparatus is used for estimating the mean arterial pressure "MAP" in the arterioles 112, the systolic blood pressure "SYS" in the arterioles, as well as the diastolic blood pressure "DIA" in the arteries 111. In this exemplifying case, the fingertip 108 is first pressed against the pressure instrument 102 so that the mechanical pressure P is above the systolic blood pressure and thus the blood flow is blocked. Thereafter, the press is slowly released so that the mechanical pressure P is ramped down as a function of time as depicted with a curve 122 shown in FIG. 1b. The curve 119 may represent for example a bandpass filtered output signal of the PPG sensor 101. The passband of the bandpass filtering can be from example from 1 Hz to 10 Hz. In this exemplifying case, the bandpass filtered signal is Hilbert transformed for forming an envelope of the bandpass filtered signal. In FIG. 1b, the Hilbert transformed filtered signal is depicted with a curve 120 and the envelope is depicted with a curve 121.

An estimate of the MAP in the arterioles 112 is the value of the mechanical pressure P where the above-mentioned envelope 121 of the reflected electromagnetic radiation reaches its maximum. Thus, the MAP in the arterioles can be estimated with the aid of the envelope curve 121 and the mechanical pressure curve 122 as shown in FIG. 1b. An estimate of the systolic blood pressure "SYS" in the arterioles 112 is the value of the mechanical pressure P which is greater than the estimated MAP in the arterioles 112 and at which the envelope of the reflected electromagnetic radiation is a predetermined percentage, typically 50%, of the maximum of the envelope. Thus, the SYS in the arterioles can be estimated with the aid of the envelope curve 121 and the mechanical pressure curve 122 as shown in FIG. 1b. The estimate of the SYS in the arterioles is also an estimate of the diastolic blood pressure "DIA" in the arteries 111.

In the exemplifying case illustrated in FIG. 1b, the mechanical pressure P is ramped down. It is however also possible that the mechanical pressure P is ramped up for estimating the MAP in the arterioles 112, the SYS in the arterioles, and the DIA in the arteries 111. In this exemplifying case, the envelope of the reflected electromagnetic radiation is a time-reversed version of the envelope 121. Furthermore, it is to be noted that the mechanical pressure P does not necessarily follow an ideal straight line as a function of time when the mechanical pressure P is ramped down or up.

An apparatus according to an exemplifying and non-limiting embodiment comprises a processing system 103 configured to determine the estimate of the MAP in the arterioles 112. In other words, the processing system 103 is configured to determine a first value of the mechanical pressure P where the above-mentioned envelope 121 of the reflected electromagnetic radiation reaches its maximum when the mechanical pressure P is ramped down or up from a start value to an end value, the first value being the estimate of the MAP in the arterioles 112. In an apparatus according to an exemplifying and non-limiting embodiment, the processing system 103 is configured to determine the estimate of the SYS in the arterioles 112 and the estimate of the DIA in the arteries 111. In other words, the processing system 103 is configured to determine a second value of the mechanical pressure P which is higher than the determined first value and at which the envelope of the reflected electromagnetic radiation is substantially a predetermined percentage, typically 50%, of the maximum of the envelope, the determined second value being the estimate of the SYS in the arterioles 112 and the estimate of the DIA in the arteries 111. It is however also possible that an apparatus according to an exemplifying and non-limiting embodiment comprises a memory for storing time-series of the output signals of the PPG sensor and the pressure sensor, and/or a transmitter for transmitting the time-series to an external device. In this exemplifying case, the above-mentioned estimates that describe functionality of an arterial system can be formed off-line with an external device, e.g. a personal computer.

Figure 1C:
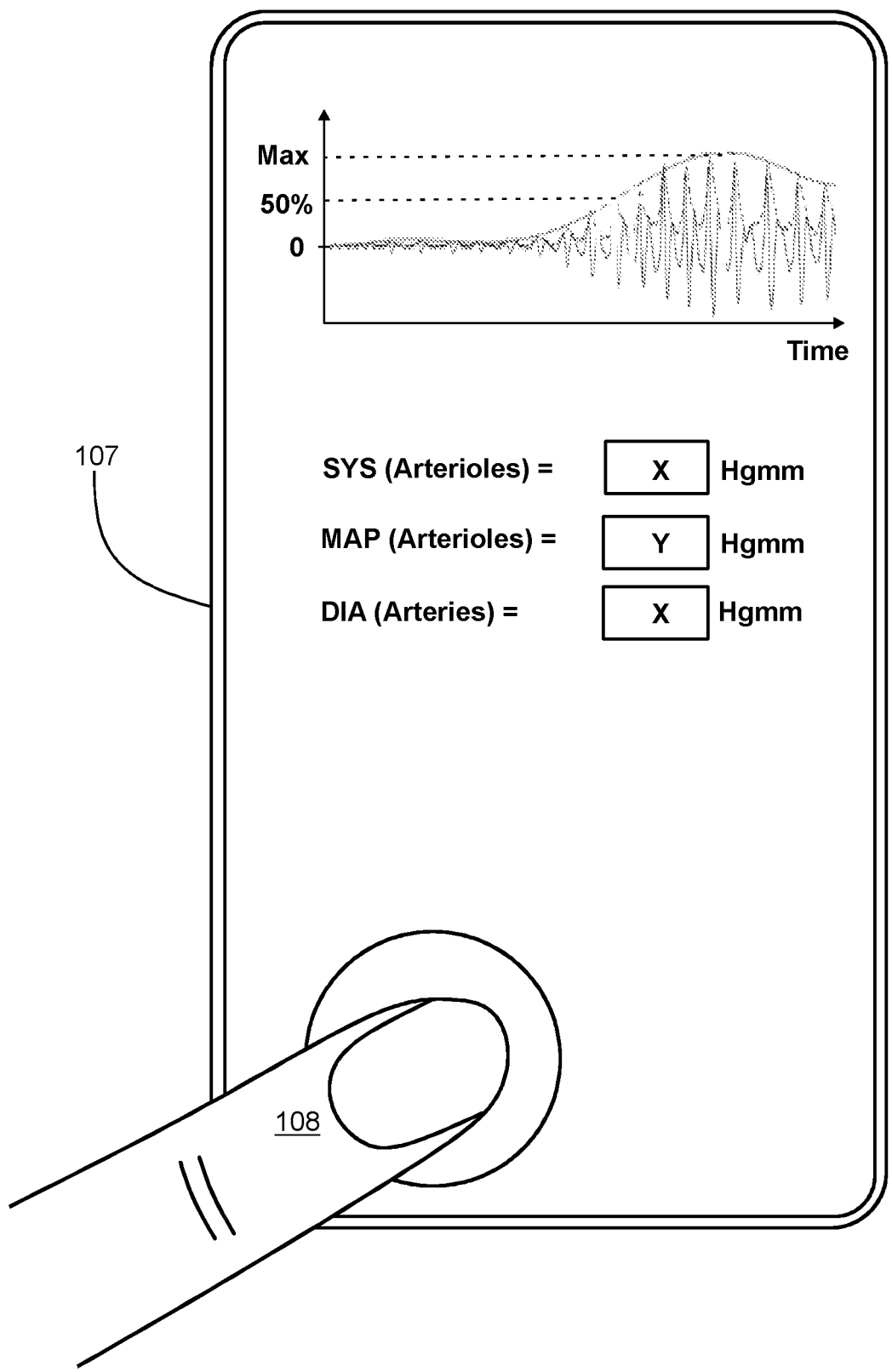
FIG. 1c shows a mobile device comprising an apparatus illustrated in FIG. 1a, FIG. 2a illustrates an apparatus according to an exemplifying and non-limiting embodiment for measuring functionality of an arterial system.

FIG. 1c shows a mobile device 107 comprising the apparatus illustrated in FIG. 1a. The mobile device 107 can be for example a mobile phone or a palmtop computer. The pressure sensor and the PPG sensor are on a surface of the mobile device so that an individual can press a fingertip 108 against the pressure sensor and the PPG sensor. In this exemplifying case, the mobile device 107 is configured to display the bandpass filtered output signal of the PPG sensor and the envelope of the bandpass filtered output signal. Furthermore, the mobile device 107 is configured to display the estimates of the SYS in the arterioles, the MAP in the arterioles, and the DIA in the arteries, where the estimates are formed with the aid of the envelope and time dependence of the mechanical pressure measured by the pressure sensor. It is also possible that an apparatus according to an exemplifying embodiment of the invention is a part of a ring, a bracelet, a wrist watch, or any other wearable device, or a combination of them, or a combination of a wearable device and a mobile phone or another mobile communication device. For example, an inner surface of a ring or a bracelet can be provided with the PPG sensor and with a pressure sensor. In this exemplifying case, a user can control the pressure by pressing the ring or bracelet against a surface of a finger or a wrist surrounded by the ring or the bracelet.

Figure 2A:
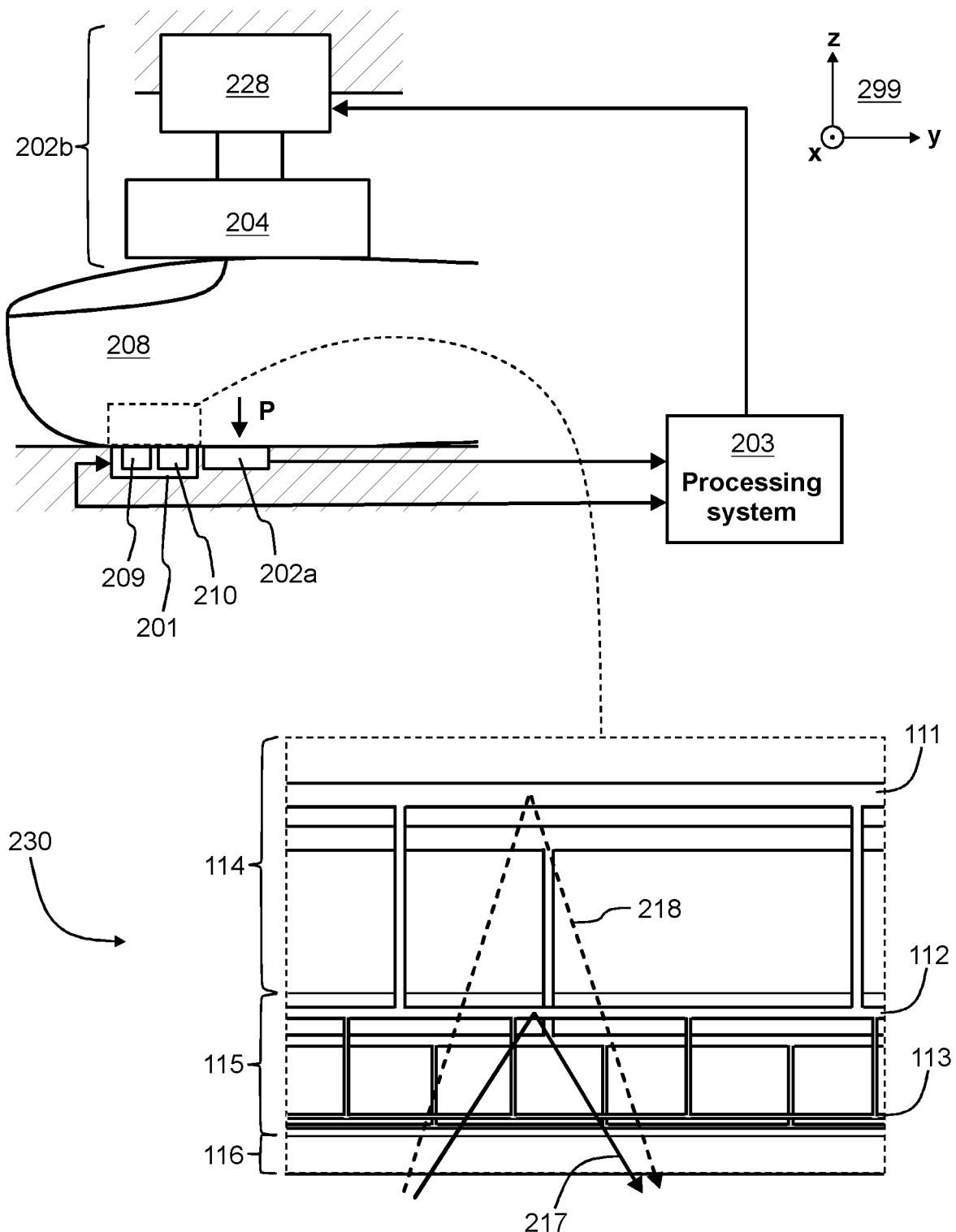
FIG. 2b shows exemplifying graphs illustrating electromagnetic radiations having different wavelengths and reflected off an arterial system of a fingertip as functions of time.

FIG. 2a shows a schematic illustration of an apparatus according to an exemplifying and non-limiting embodiment for measuring functionality of an arterial system. The apparatus comprises a photoplethysmography "PPG" sensor 201 for emitting, to a fingertip 208 of an individual, first electromagnetic radiation having a wavelength in the range from 475 nm to 600 nm and second electromagnetic radiation having a wavelength in the range from 620 nm to 900 nm, and for receiving parts of the first and second electromagnetic radiations reflected off the arterial system of the fingertip 208. The wavelength of the first electromagnetic radiation can be, for example but not necessarily, circa 537 nm in which case the first electromagnetic radiation is green light. In an apparatus according to an exemplifying and non-limiting embodiment, the wavelength of the second electromagnetic radiation is in the range from 650 nm to 890 nm. The wavelength of the second electromagnetic radiation can be, for example but not necessarily, circa 660 nm in which case the second electromagnetic radiation is red light or circa 880 nm in which case the second electromagnetic radiation is infrared "IR" radiation. It is also possible that the PPG sensor 201 is configured to emit and measure electromagnetic radiation with three or more different wavelengths. The PPG sensor 201 comprises a radiation emitter 209 and a photodetector 210. The radiation emitter 209 may comprise e.g. light emitting diodes "LED" and the photodetector 110 may comprise e.g. wavelength sensitive photodiodes or phototransistors. FIG. 2a shows also a magnified, schematic section view 230 of the fingertip. The section plane is parallel with the yz-plane of a coordinate system 299. In the section view 230, the first emitted and reflected electromagnetic radiation is depicted with a polyline 217 and the second emitted and reflected electromagnetic radiation is depicted with a polyline 218. As illustrated in the section view 230, the first electromagnetic radiation 217 does not reach arteries 111 located in the hypodermis 114 but can only reach arterioles 112 located in the reticular dermis 115 whereas the second electromagnetic radiation 218 can reach the arteries 111. In the section view 230, capillaries are denoted with a reference 113 and the epidermis of the skin of the fingertip is denoted with a reference 116.

The apparatus further comprises a pressure instrument for managing mechanical pressure applied on the arterial system when the PPG sensor 201 emits and receives the above-mentioned first and second electromagnetic radiations. In this exemplifying case, the pressure instrument comprises a pressure sensor 202a for measuring mechanical pressure P directed by the fingertip 208 to the pressure sensor and pressing means 202b for controllably pressing the fingertip 208 against the PPG sensor 201 and the pressure sensor 202a. In this exemplifying apparatus, the pressing means comprise a pressing element 204 and force generating means 228 for directing force to the pressing element 204. The force generating means 228 may comprise for example an electric stepper motor and a threaded rod.

Figure 2B:
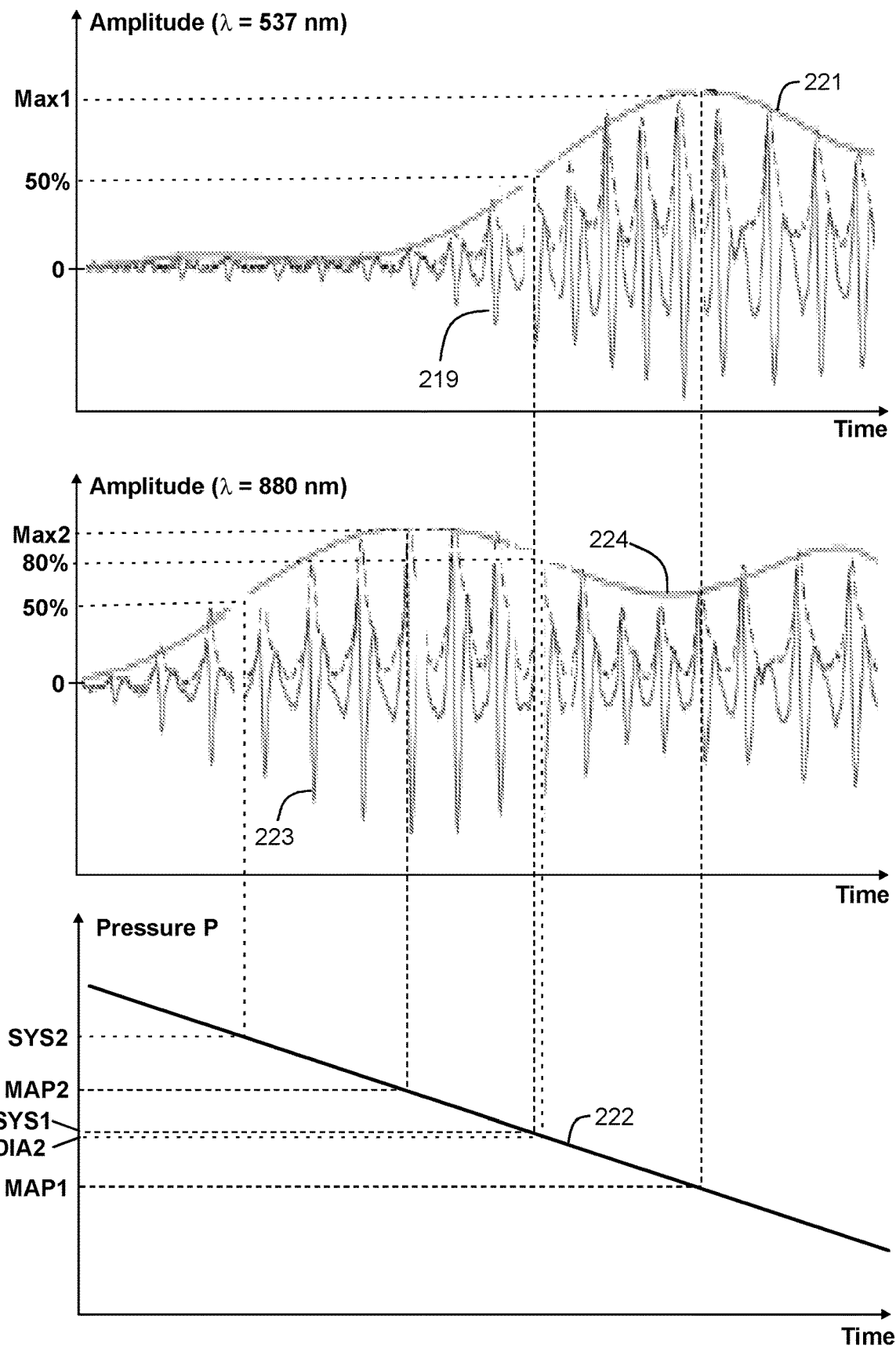

FIG. 2b shows a curve 219 that illustrates the reflected first electromagnetic radiation and a curve 223 that illustrates the reflected second electromagnetic radiation in an exemplifying situation where the apparatus is used for estimating the mean arterial pressure "MAP1" in the arterioles 112, the mean arterial pressure "MAP2" in the arteries 111, the systolic blood pressure "SYS1" in the arterioles, the systolic blood pressure "SYS2" in the arteries, and the diastolic blood pressure "DIA2" in the arteries. In this exemplifying case, the fingertip 208 is first pressed against the pressure sensor 202a so that the mechanical pressure P is above the systolic blood pressure and thus the blood flow is blocked. Thereafter, the press is slowly released so that the mechanical pressure P is ramped down as a function of time as depicted with a curve 222 shown in FIG. 2b. The curves 219 and 223 may represent for example bandpass filtered output signals of the PPG sensor 201. The passband of the bandpass filtering can be e.g. from 1 Hz to 10 Hz. In this exemplifying case, the bandpass filtered signals are Hilbert transformed for forming envelopes of the bandpass filtered signals. In FIG. 2b, the Hilbert transformed filtered signals are depicted with dashed line curves. The envelope of the reflected first electromagnetic radiation is depicted with a curve 221, and the envelope of the reflected second electromagnetic radiation is depicted with a curve 224.

As shown by FIG. 2b, the estimate of the MAP1 is the value of the mechanical pressure P where the envelope 221 reaches its maximum, the estimate of the MAP2 is the value of the mechanical pressure P where the envelope 224 reaches its maximum, the estimate of the SYS1 is the value of the mechanical pressure P which is greater than the MAP1 and at which the envelope 221 is 50% of the maximum of the envelope 221, the estimate of the SYS2 is the value of the mechanical pressure P which is greater than the MAP2 and at which the envelope 224 is 50% of the maximum of the envelope 224, and the estimate of the DIA2 is the value of the mechanical pressure P which is less than the MAP2 and at which the envelope 224 is 80% of the maximum of the envelope 224. As the systolic blood pressure SYS1 in the arterioles is substantially equal to the diastolic blood pressure DIA2 in the arteries, the estimate of the SYS1 acts as another estimate for the diastolic blood pressure in the arteries. A final estimate for the diastolic blood pressure in the arteries can be for example a weighted average of the estimate based on the envelope 224 and the estimate based on the envelope 221.

An apparatus according to an exemplifying and non-limiting embodiment comprises a processing system 203 configured to control the force generating means 228 so that the mechanical pressure P has a desired behavior as a function of time, e.g. such as depicted with the curve 222 in FIG. 2b. Furthermore, the processing system 203 can be configured to form the above-mentioned estimates with the aid of the output signals of the PPG sensor 201 and the output signal of the pressure sensor 202b.

Figure 3:
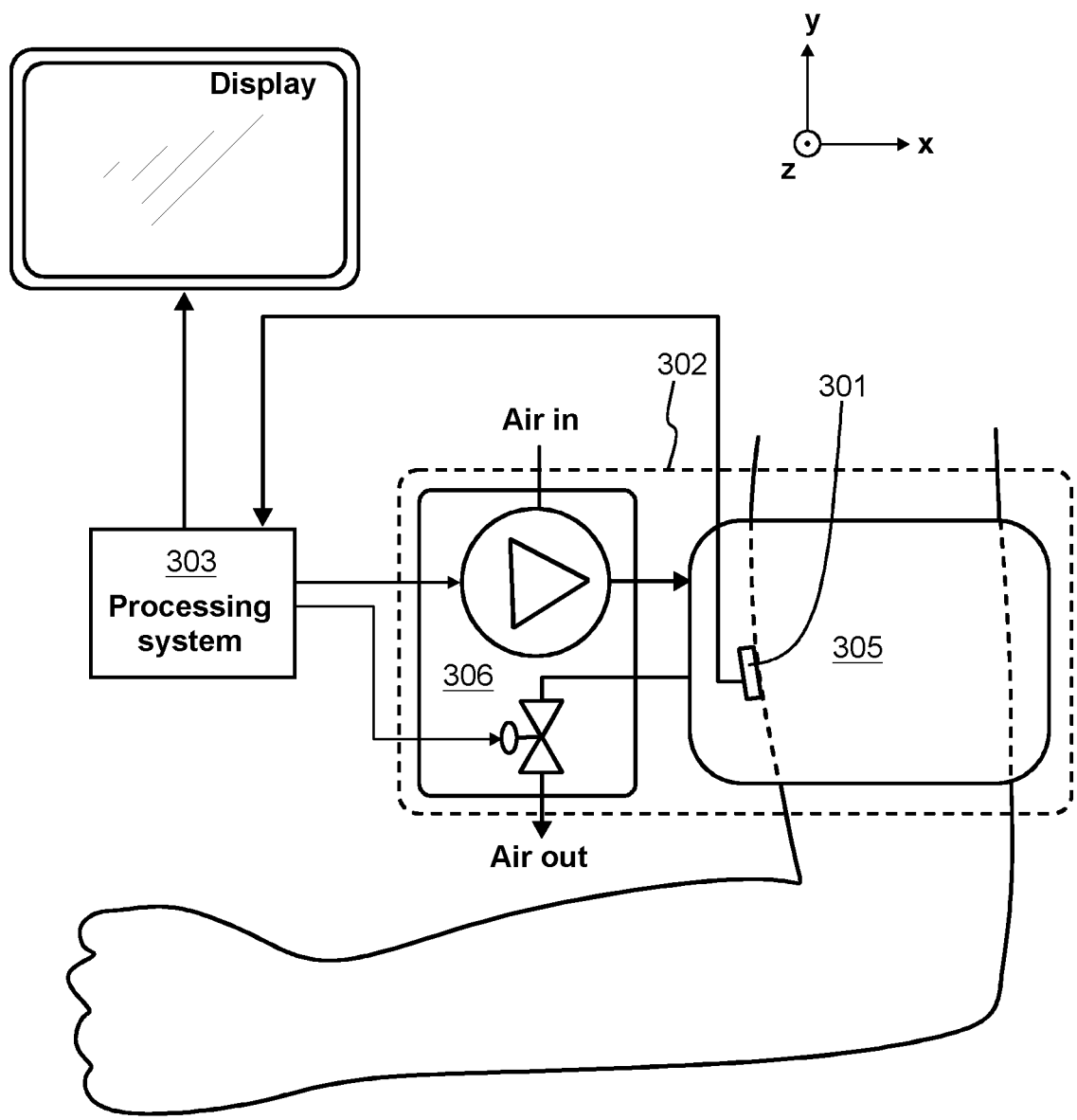
FIG. 3 illustrates an apparatus according to an exemplifying and non-limiting embodiment for measuring functionality of an arterial system.

FIG. 3 shows a schematic illustration of an apparatus according to an exemplifying and non-limiting embodiment for measuring functionality of an arterial system. The apparatus comprises a photoplethysmography "PPG" sensor 301 for emitting, to the arterial system, electromagnetic radiation having a wavelength in the range from 475 nm to 600 nm and for receiving a part of the electromagnetic radiation reflected off the arterial system. The wavelength can be for example circa 515 nm. The apparatus comprises a pressure instrument 302 for managing mechanical pressure applied on the arterial system when the photoplethysmography sensor 301 emits and receives the electromagnetic radiation to and from the arterial system. In this exemplifying case, the pressure instrument 302 comprises a pressing device 305 for directing controllable mechanical pressure to the brachial artery. The pressing device 305 can be for example a cuff and the apparatus may comprise a pump system 306 for controlling gas, e.g. air, pressure inside the cuff to direct the controllable mechanical pressure to the brachial artery. It is however also possible that the pressing device comprises e.g. a flexible belt that is tightened around the upper arm. The PPG sensor 301 is located on a surface of the pressing device 305 so that the PPG sensor 301 can be placed on top of the brachial artery. The brachial artery can be found by e.g. palpation. According to experiments, an output signal of the PPG sensor 301 does not show pulsatile waveform when the mechanical pressure is above diastolic blood pressure and the output signal of the PPG sensor 301 starts showing pulsatile waveform when the mechanical pressure is lowered under the diastolic blood pressure. Thus, the apparatus can be used for direct measurement of the diastolic blood pressure.

An apparatus according to an exemplifying and non-limiting embodiment comprises a processing system 303 configured to control the pressing device 305 so that the mechanical pressure has a desired behavior as a function of time. In the exemplifying case shown in FIG. 3, the processing system 303 is configured to control the pump system 306 so that the mechanical pressure produced by the cuff has a desired behavior as a function of time. Furthermore, the processing system 303 can be configured to determine a value of the mechanical pressure at which the output signal of the PPG sensor 301 starts showing pulsatile waveform.

Figure 4A:
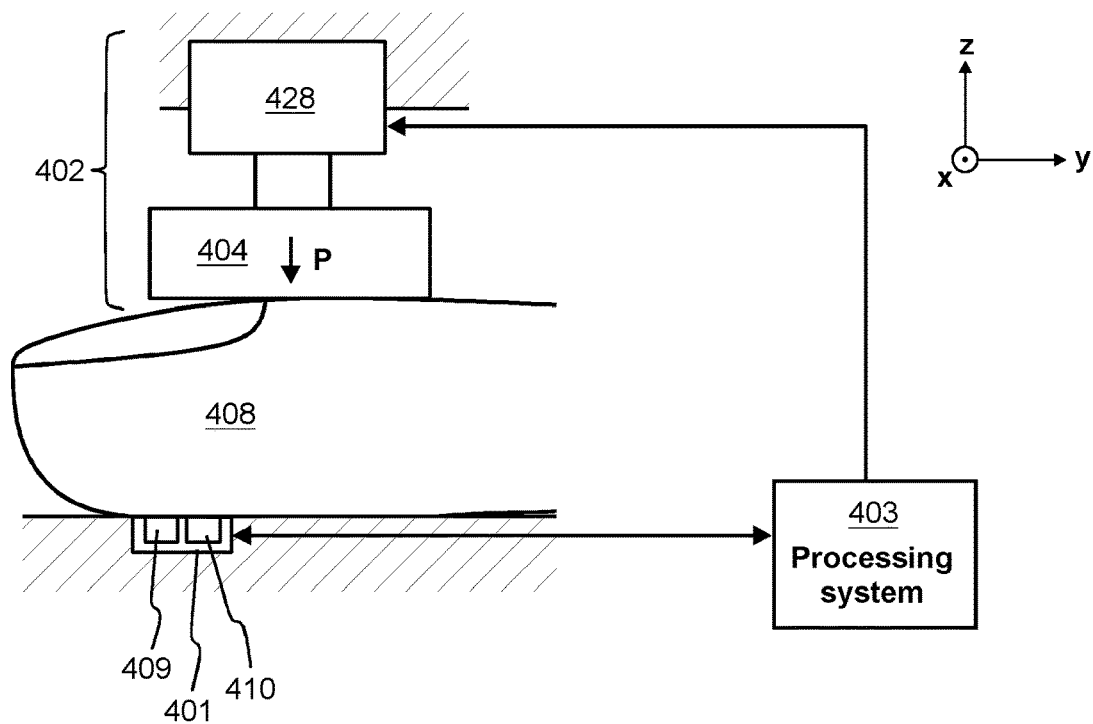
FIG. 4a illustrates an apparatus according to an exemplifying and non-limiting embodiment for measuring functionality of an arterial system.

FIG. 4a shows a schematic illustration of an apparatus according to an exemplifying and non-limiting embodiment for measuring functionality of an arterial system. The apparatus comprises a photoplethysmography "PPG" sensor 401 for emitting, to a fingertip 408 of an individual, first electromagnetic radiation having a wavelength in the range from 475 nm to 600 nm and second electromagnetic radiation having a wavelength in the range from 620 nm to 900 nm, and for receiving parts of the first and second electromagnetic radiations reflected off the arterial system of the fingertip 408. The wavelength of the first electromagnetic radiation can be, for example but not necessarily, circa 537 nm in which case the first electromagnetic radiation is green light. The wavelength of the second electromagnetic radiation can be for example circa 660 nm in which case the second electromagnetic radiation is red light or circa 880 nm in which case the second electromagnetic radiation is infrared "IR" radiation. The PPG sensor 401 comprises a radiation emitter 409 and a photodetector 410.

The apparatus further comprises a pressure instrument 402 for managing mechanical pressure applied on the arterial system when the PPG sensor 401 emits and receives the first and second electromagnetic radiation to and from the fingertip 408. In this exemplifying case, the pressure instrument 402 comprises a pressing element 404 for pressing the fingertip 408 and force generating means 428 for directing force to the pressing element 404.

Figure 4B:
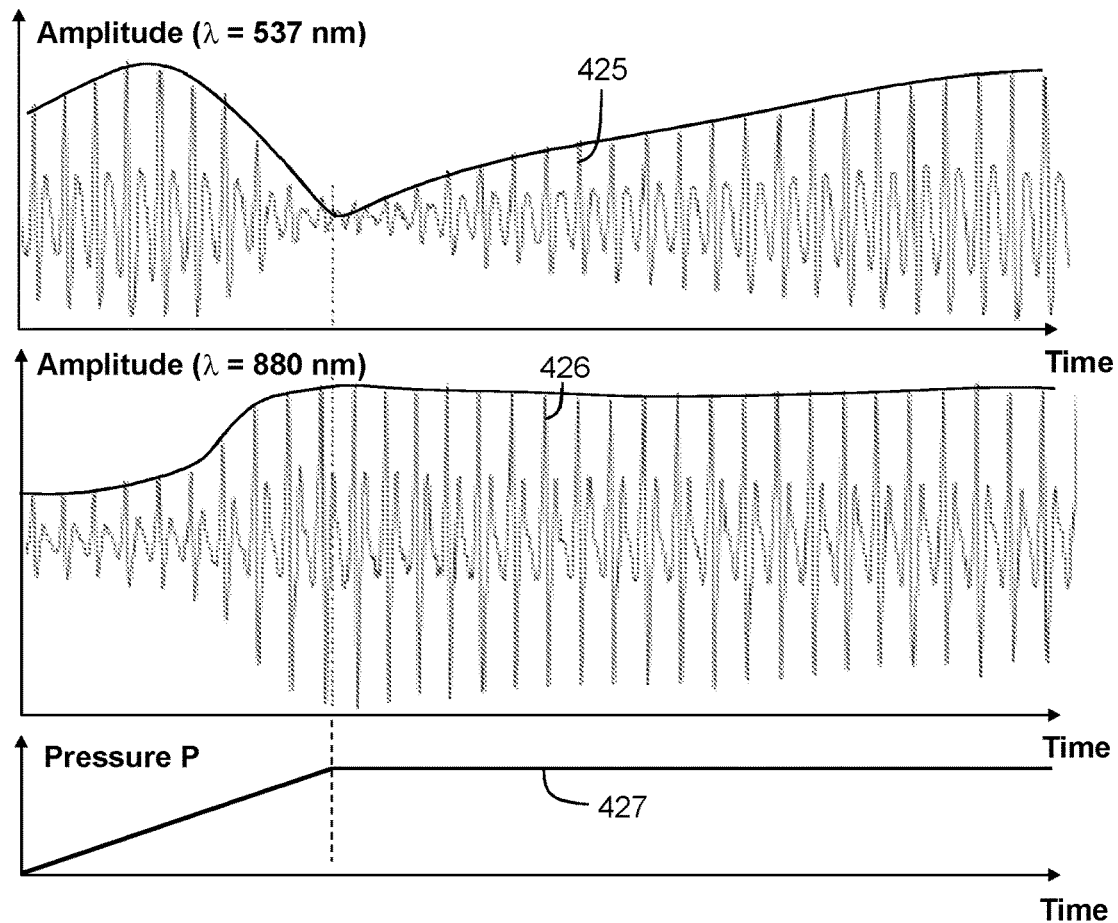
FIG. 4b shows exemplifying graphs illustrating electromagnetic radiations having different wavelengths and reflected off an arterial system of a fingertip as functions of time.

FIG. 4b shows a curve 425 that illustrates the reflected first electromagnetic radiation and a curve 426 that illustrates the reflected second electromagnetic radiation in an exemplifying situation where the pressure instrument 402 first increases the mechanical pressure and then keeps the mechanical pressure substantially constant. The curves 425 and 426 can depict for example bandpass filtered output signals of the PPG sensor 401. The passband of the bandpass filtering can be from example from 1 Hz to 10 Hz. The mechanical pressure as a function of time is depicted with a curve 427 shown in FIG. 4b. As shown by FIG. 4b, the mechanical pressure is increased up to a point at which the pulsatile waveform of the reflected first electromagnetic radiation drops near to zero and the pulsatile waveform of the reflected second electromagnetic radiation reaches its maximum. The low pulsatile waveform of the reflected first electromagnetic radiation indicates near occlusion of arterioles suggesting near systolic arteriole pressure. Tangential stress caused by small flow triggers excretion of nitric oxide "NO" in endothelial cells, which then causes vasodilation in the arterioles letting more blood flow in them. When the applied mechanical pressure is kept constant, the pulsatile waveform of the reflected first electromagnetic radiation increases as illustrated by the curve 425. The above-described increase in the pulsatile waveform of the reflected first electromagnetic radiation suggests normal endothelial function, whereas a lack of increase suggests endothelial dysfunction.

An apparatus according to an exemplifying and non-limiting embodiment comprises a processing system 403 for controlling the pressure instrument 402 to increase the mechanical pressure until an envelope of the reflected first electromagnetic radiation drops down to substantially zero and subsequently to keep the mechanical pressure constant.

In an apparatus according to another exemplifying and non-limiting embodiment, the processing system 403 is configured to control the pressure instrument 402 to increase the mechanical pressure until an envelope of the reflected second electromagnetic radiation reaches its maximum and subsequently to keep the mechanical pressure constant. The force generating means 428 may comprise for example a threaded rod and an electric stepper motor controlled by the processing system 403. The mechanical pressure can be increased by running the electric stepper motor in an appropriate direction of rotation, and the mechanical pressure can be kept constant by keeping the electric stepper motor stationary. In an apparatus according to an exemplifying and non-limiting embodiment, the processing system 403 is configured to detect whether the envelope of the reflected first electromagnetic radiation increases when the mechanical pressure is kept constant.

Each of the processing systems 103, 203, 303, and 403 shown in FIGS. 1a, 2a, 3, and 4a can be implemented for example with one or more processor circuits, each of which can be a programmable processor circuit provided with appropriate software, a dedicated hardware processor such as for example an application specific integrated circuit "ASIC", or a configurable hardware processor such as for example a field programmable gate array "FPGA". Each of the processing systems 103, 203, 303, and 403 may further comprise memory implemented for example with one or more memory circuits each of which can be e.g. a random-access memory "RAM" device.

Figure 5:
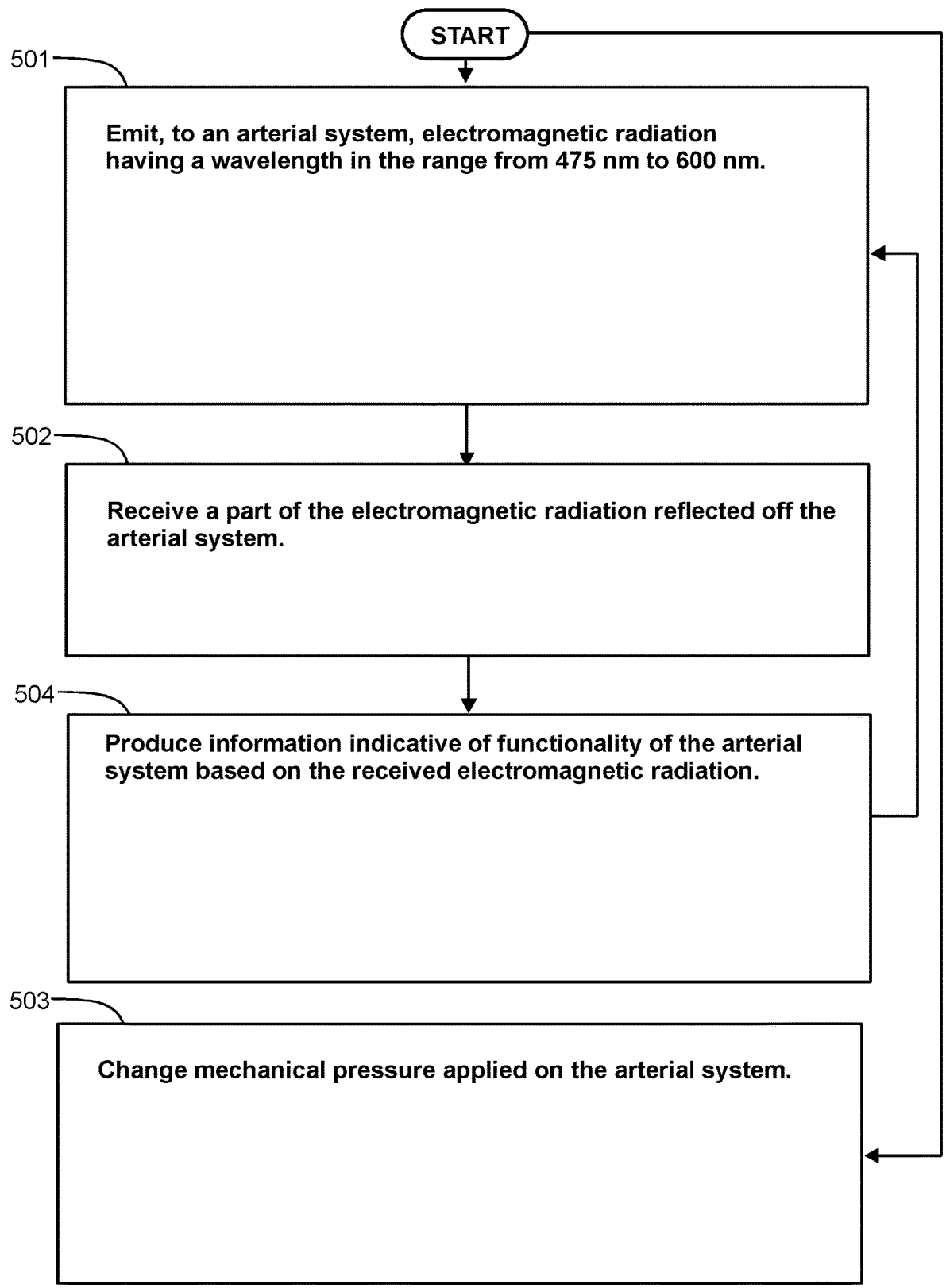
FIG. 5 shows a flowchart of a method according to an exemplifying and non-limiting embodiment for measuring functionality of an arterial system.

FIG. 5 shows a flowchart of a method according to an exemplifying and non-limiting embodiment for measuring functionality of an arterial system of an individual. The method comprises the following actions:
- action 501: emitting, to the arterial system, electromagnetic radiation having a wavelength in a range from 475 nm to 600 nm,
- action 502: receiving a part of the electromagnetic radiation reflected off the arterial system, and
- action 503: changing mechanical pressure applied on the arterial system when the electromagnetic radiation is emitted to the arterial system and the reflected electromagnetic radiation is received from the arterial system, and
- action 504: producing information indicative of the functionality of the arterial system based on the received electromagnetic radiation.

In a method according to an exemplifying and non-limiting embodiment the wavelength of the electromagnetic radiation is in the range from 480 nm to 600 nm.

In a method according to an exemplifying and non-limiting embodiment, the wavelength of the electromagnetic radiation is in the range from 500 nm to 600 nm.

In a method according to an exemplifying and non-limiting embodiment, the wavelength of the electromagnetic radiation is in the range from 500 nm to 575 nm In a method according to an exemplifying and non-limiting embodiment, the wavelength of the electromagnetic radiation is in the range from 500 nm to 550 nm.

A method according to an exemplifying and non-limiting embodiment comprises determining a first value of the mechanical pressure at which an envelope of the reflected electromagnetic radiation reaches its maximum when the mechanical pressure is ramped down or up from a start value to an end value. The determined first value is indicative of the mean arterial pressure "MAP" of arterioles of the arterial system.

A method according to an exemplifying and non-limiting embodiment comprises determining a second value of the mechanical pressure which is higher than the determined first value and at which the envelope of the reflected electromagnetic radiation is substantially a predetermined percentage e.g. 50% of the maximum of the envelop. The determined second value is indicative of the diastolic blood pressure "DIA" of arteries of the arterial system as well as the systolic blood pressure "SYS" of the arterioles of the arterial system.

A method according to an exemplifying and non-limiting embodiment comprises increasing the mechanical pressure until the envelope of the reflected electromagnetic radiation drops down to substantially zero and subsequently keeping the mechanical pressure constant. Furthermore, the method according to this exemplifying and non-limiting embodiment comprises detecting whether the envelope of the reflected electromagnetic radiation increases when the mechanical pressure is kept constant. An increase in the envelope is indicative of normal endothelial function of the arterial system, whereas a lack of increase in indicative of endothelial dysfunction.

A method according to an exemplifying and non-limiting embodiment comprises directing the mechanical pressure to a fingertip of the individual when the electromagnetic radiation is emitted and received to and from the fingertip.

A method according to an exemplifying and non-limiting embodiment comprises measuring the pressure directed to the fingertip when the electromagnetic radiation is emitted and received to and from the fingertip.

A method according to an exemplifying and non-limiting embodiment comprises controlling gas pressure inside a cuff surrounding an upper arm of the individual to direct the mechanical pressure to the brachial artery of the individual when the electromagnetic radiation is emitted and received to and from an area of the upper arm on top of the brachial artery.

In a method according to an exemplifying and non-limiting embodiment, the above-mentioned electromagnetic radiation having the wavelength in the range from 475 nm to 600 nm is first electromagnetic radiation, and the method according to this exemplifying and non-limiting embodiment comprises:
- emitting, to the arterial system, second electromagnetic radiation having a wavelength in the range from 620 nm to 900 nm, and
- receiving a part of the second electromagnetic radiation reflected off the arterial system.

In a method according to an exemplifying and non-limiting embodiment, the wavelength of the second electromagnetic radiation is the range from 650 nm to 890 nm.

A method according to an exemplifying and non-limiting embodiment comprises determining a third value of the mechanical pressure at which an envelope of the reflected second electromagnetic radiation reaches its maximum when the mechanical pressure is ramped down or up from a start value to an end value. The determined third value is indicative of mean arterial pressure "MAP" of arteries of the arterial system.

A method according to an exemplifying and non-limiting embodiment comprises determining a fourth value of the mechanical pressure which is higher than the determined third value and at which the envelope of the reflected second electromagnetic radiation is substantially a first predetermined percentage, e.g. 50%, of the maximum of the envelope of the reflected second electromagnetic radiation. The determined fourth value is indicative of systolic blood pressure "SYS" of arteries of the arterial system.

A method according to an exemplifying and non-limiting embodiment comprises determining a fifth value of the mechanical pressure which is lower than the determined third value and at which the envelope of the reflected second electromagnetic radiation is substantially a second predetermined percentage, e.g. 80%, of the maximum of the envelope of the reflected second electromagnetic radiation. The determined fifth value is indicative of diastolic blood pressure "SYS" of arteries of the arterial system.

A method according to an exemplifying and non-limiting embodiment comprises increasing the mechanical pressure until the envelope of the reflected second electromagnetic radiation reaches its maximum and subsequently keeping the mechanical pressure constant. Furthermore, the method according to this exemplifying and non-limiting embodiment comprises detecting whether the envelope of the reflected first electromagnetic radiation increases when the mechanical pressure is kept constant. An increase in the envelope of the reflected first electromagnetic radiation is indicative of normal endothelial function of the arterial system.

A computer program according to an exemplifying and non-limiting embodiment comprises computer executable instructions for controlling a programmable processing system to carry out actions related to a method according to any of the above-described exemplifying and non-limiting embodiments.

A computer program according to an exemplifying and non-limiting embodiment comprises software modules for measuring functionality of an arterial system of an individual. The software modules comprise computer executable instructions for controlling a programmable processing system to:
- control a photoplethysmography "PPG" sensor to emit, to the arterial system, electromagnetic radiation having a wavelength in a range from 475 nm to 600 nm, and to receive a part of the electromagnetic radiation reflected off the arterial system, and
- control a pressure instrument to manage mechanical pressure applied on the arterial system when the PPG sensor emits and receives the electromagnetic radiation to and from the arterial system.

The software modules can be for example subroutines or functions implemented with programming tools suitable for the programmable processing equipment.

In a computer program according to an exemplifying and non-limiting embodiment, the software modules comprise computer executable instructions for controlling the programmable processing system to control the pressure instrument to change the mechanical pressure applied on the arterial system when the PPG sensor emits and receives the electromagnetic radiation to and from the arterial system.

A computer program product according to an exemplifying and non-limiting embodiment comprises a computer readable medium, e.g. a compact disc "CD", encoded with a computer program according to an exemplifying embodiment.

A signal according to an exemplifying and non-limiting embodiment is encoded to carry information defining a computer program according to an exemplifying embodiment.

A computer program according to an exemplifying and non-limiting embodiment may constitute e.g. a part of a software of a mobile device, e.g. a smart phone or a wearable device.

The specific examples provided in the description given above should not be construed as limiting the scope and/or the applicability of the appended claims. Lists and groups of examples provided in the description given above are not exhaustive unless otherwise explicitly stated.

What is claimed is:

1. An apparatus for measuring functionality of an arterial system of an individual, the apparatus comprising a photoplethysmography sensor for emitting, to the arterial system, electromagnetic radiation having a wavelength in a range from 475 nm to 600 nm and for receiving a part of the electromagnetic radiation reflected off the arterial system, wherein the apparatus further comprises a pressure instrument for managing mechanical pressure applied on the arterial system when the photoplethysmography sensor emits and receives the electromagnetic radiation to and from the arterial system, and the pressure instrument is suitable for changing the mechanical pressure applied on the arterial system when the photoplethysmography sensor emits and receives the electromagnetic radiation to and from the arterial system, and the apparatus comprises a processing system for controlling the pressure instrument to increase the mechanical pressure until an envelope of the reflected electromagnetic radiation drops down to substantially zero and subsequently to keep the mechanical pressure constant, wherein the processing system is configured to detect whether the envelope of the reflected electromagnetic radiation increases when the mechanical pressure is kept constant, an increase of the envelope being indicative of normal endothelial function of the arterial system.

2. An apparatus according to claim 1, wherein the pressure instrument comprises a pressing element for directing the mechanical pressure to a fingertip of the individual and for changing the mechanical pressure when the photoplethysmography sensor emits and receives the electromagnetic radiation to and from the fingertip.

3. An apparatus according to claim 1, wherein the apparatus comprises a processing system for determining a first value of the mechanical pressure at which an envelope of the reflected electromagnetic radiation reaches a maximum when the mechanical pressure is ramped from a start value to an end value, the determined first value being indicative of mean arterial pressure of arterioles of the arterial system.

4. An apparatus according to claim 3, wherein the processing system is configured to determine a second value of the mechanical pressure which is higher than the determined first value and at which the envelope of the reflected electromagnetic radiation is substantially a predetermined percentage of the maximum, the determined second value being indicative of diastolic blood pressure of arteries of the arterial system as well as systolic blood pressure of the arterioles of the arterial system.

5. An apparatus according to claim 1, wherein the pressure instrument comprises a pressure sensor for measuring pressure directed by a fingertip of the individual to the pressure sensor when the photoplethysmography sensor emits and receives the electromagnetic radiation to and from the fingertip.

6. An apparatus according to claim 5, wherein the apparatus is a part of a mobile device and the pressure sensor and the photoplethysmography sensor are on a surface of the mobile device.

7. An apparatus according to claim 1, wherein the wavelength of the electromagnetic radiation is in the range from 500 nm to 600 nm.

8. An apparatus according to claim 1, wherein the wavelength of the electromagnetic radiation is in the range from 500 nm to 550 nm.

9. An apparatus according to claim 1, wherein the electromagnetic radiation having the wavelength in the range from 475 nm to 600 nm is first electromagnetic radiation, and the photoplethysmography sensor is configured to emit, to the arterial system, second electromagnetic radiation having a wavelength in a range from 620 nm to 900 nm and to receive a part of the second electromagnetic radiation reflected off the arterial system.

10. An apparatus according to claim 9, wherein the apparatus comprises a processing system for determining a first value of the mechanical pressure at which an envelope of the reflected second electromagnetic radiation reaches a maximum when the mechanical pressure is ramped from a start value to an end value, the determined first value being indicative of mean arterial pressure of arteries of the arterial system.

11. An apparatus according to claim 10, wherein the processing system is configured to determine a second value of the mechanical pressure which is higher than the determined first value and at which the envelope of the reflected second electromagnetic radiation is substantially a first predetermined percentage of the maximum of the envelope of the reflected second electromagnetic radiation, the determined second value being indicative of systolic blood pressure of arteries of the arterial system.

12. An apparatus according to claim 11, wherein the apparatus comprises a processing system for controlling the pressure instrument to increase the mechanical pressure until a maximum of the envelope of the reflected second electromagnetic radiation is reached and subsequently to keep the mechanical pressure constant.

13. An apparatus according to claim 1, wherein the pressure instrument comprises a pressing device for directing the mechanical pressure to a brachial artery of the individual, and wherein the photoplethysmography sensor is located on a surface of the pressing device intended to be on top of the brachial artery.

14. An apparatus according to claim 13, wherein the pressing device is a cuff and the pressure instrument comprises a pump system for controlling gas pressure inside the cuff to direct the mechanical pressure to the brachial artery, and wherein the photoplethysmography sensor is located on an inner surface of the cuff.

15. A method for measuring functionality of an arterial system of an individual, the method comprising:
emitting, to the arterial system, electromagnetic radiation having a wavelength in a range from 475 nm to 600 nm,
receiving a part of the electromagnetic radiation reflected off the arterial system,
changing mechanical pressure applied on the arterial system when the electromagnetic radiation is emitted to the arterial system and the reflected electromagnetic radiation is received from the arterial system so that the mechanical pressure is increased until an envelope of the reflected electromagnetic radiation drops down to substantially zero,
keeping the mechanical pressure constant after the envelope of the reflected electromagnetic radiation has dropped down to substantially zero, and
detecting whether the envelope of the reflected electromagnetic radiation increases when the mechanical pressure is kept constant, an increase of the envelope being indicative of normal endothelial function of the arterial system.

16. A non-transitory computer readable medium encoded with a computer program comprising computer executable instructions for controlling a programmable processing system to:
control a photoplethysmography sensor to emit, to an arterial system, electromagnetic radiation having a wavelength in a range from 475 nm to 600 nm, and to receive a part of the electromagnetic radiation reflected off the arterial system,
control a pressure instrument to manage mechanical pressure applied on the arterial system when the photoplethysmography sensor emits and receives the electromagnetic radiation to and from the arterial system so that the mechanical pressure is increased until an envelope of the reflected electromagnetic radiation drops down to substantially zero,
keep the mechanical pressure constant after the envelope of the reflected electromagnetic radiation has dropped down to substantially zero, and
detect whether the envelope of the reflected electromagnetic radiation increases when the mechanical pressure is kept constant, an increase of the envelope being indicative of normal endothelial function of the arterial system.

* * * * *